United States Patent [19]
Jarvinen et al.

[11] Patent Number: 5,512,685
[45] Date of Patent: Apr. 30, 1996

[54] PROCESS FOR THE PREPARATION OF 3-SUBSTITUTED THIOPHENES

[75] Inventors: Hannele Jarvinen; Leila Lahtinen, both of Helsinki; Osmo Hormi, Oulu; Jan Nasman, Turku; Anna-Liisa Tammi, Paimio, all of Finland

[73] Assignee: Neste Oy, Porvoo, Finland

[21] Appl. No.: 244,379

[22] PCT Filed: Dec. 8, 1992

[86] PCT No.: PCT/FI92/00333

§ 371 Date: Dec. 20, 1994

§ 102(e) Date: Dec. 20, 1994

[87] PCT Pub. No.: WO93/12106

PCT Pub. Date: Jun. 24, 1993

[30] Foreign Application Priority Data

Dec. 9, 1991 [FI] Finland ..................... 915785

[51] Int. Cl.⁶ .................. C07D 333/06; C07D 333/02
[52] U.S. Cl. ................... 549/86; 549/29; 549/83
[58] Field of Search ................... 549/86, 84, 80, 549/29, 255

[56] References Cited

U.S. PATENT DOCUMENTS

| | | | |
|---|---|---|---|
| 2,658,903 | 11/1953 | Tullar et al. ................ | 549/83 |
| 3,933,856 | 1/1976 | Khairullin et al. ................ | 549/83 |
| 4,282,156 | 8/1981 | Gutierrez ................ | 562/590 |
| 4,581,464 | 4/1986 | Ross et al. ................ | 549/255 |
| 4,599,432 | 7/1986 | Kuroda et al. ................ | 549/255 |

FOREIGN PATENT DOCUMENTS

| | | |
|---|---|---|
| 0038121 | 10/1981 | European Pat. Off. . |
| 0299586 | 1/1989 | European Pat. Off. . |
| 0359316 | 3/1990 | European Pat. Off. . |
| 1006957 | 9/1974 | Japan . |
| 9217465 | 10/1992 | WIPO . |

OTHER PUBLICATIONS

Wolf et al, Organic Reactions, Chapter 9, The preparation of thiophenes and tetrathiophenes, Merck & Co. Inc, vol. VI, pp. 410–468, 1951.

March J., Advanced Organic Chemistry, pp. 347, 691–692, 1985.

Butler et al., 197 *J. Chem. Soc.* (*B*) 852–854 (1970).

Butler et al., 197 *J. Chem. Soc.* (*B*) 848–851 (1970).

Butler et al., 197 *J. Chem. Soc.* (*B*) 170–173 (1970).

E. Campaigne et al., 76 *J. Am. Chem. Soc.* 2445–2447 (1954).

F. Duus, 32 *Tetrahedron* 2817–2825 (1976).

*Primary Examiner*—Allen J. Robinson
*Assistant Examiner*—Deborah Lambkin
*Attorney, Agent, or Firm*—Birch, Stewart, Kolasch & Birch

[57] ABSTRACT

The invention relates to a process for the preparation of 3-substituted thiophenes in which the substituent is a $C_4$–$C_{18}$-alkyl group. According to the invention, the preparation is carried out by allowing an alkali metal salt of a $C_4$–$C_{18}$-alkyl-succinic acid to react with a compound of sulfur and phosphorus, e.g. tetraphosphorus decasulfide, in an organic solvent at a temperature of 100°–180° C., the product obtained being 3-($C_4$–$C_{18}$-alkyl)thiophene. The said reaction may be the last step in a process in which the initial material is maleic acid anhydride with which $\alpha$-$C_4$–$C_{18}$-alkene is combined so that $C_4$–$C_{18}$-alkenylsuccinic acid anhydride is obtained, whereafter this is hydrogenated catalytically to produce $C_4$–$C_{18}$-alkylsuccinic acid anhydride. This is thereafter reacted with an alkali metal hydroxide so that an alkali salt of the $C_4$–$C_{18}$-alkylsuccinic acid is obtained, which salt is reacted with a compound of sulfur and phosphorus to produce 3-($C_4$–$C_{18}$-alkyl)thiophene, which constitutes the final product.

19 Claims, No Drawings

PROCESS FOR THE PREPARATION OF 3-SUBSTITUTED THIOPHENES

BACKGROUND OF THE INVENTION

1. Field of the Invention

The invention relates to a process for the preparation of 3-substituted thiophenes in which the substituent consists of a $C_4$–$C_{18}$ alkyl group.

2. Description of the Related Art

It is known that the preparation of 3-substituted thiophenes is more difficult than the preparation of 2-substituted thiophenes. However, 3-substituted thiophenes are a desirable intermediate or final product in various applications, for example as an herbicide or a fungicide. Certain 3-substituted thiophenes can also be used as monomers in the preparation of, for example, electrically conductive polymers.

3-substituted thiophenes can, in principle, be prepared in two different ways: by using as the initial material a thiophene or a thiophene provided with a modifiable 3-substituent, or by using as the initial material an acyclic compound. Substituted thiophenes can, of course, also be prepared by other methods, but in that case the products are usually 2-substituted.

The best known way of using thiophene as the initial material is the bromination of thiophene. 3-Bromothiophene can be prepared, for example according to EP publication 299 586, catalytically from 2,5-dibromothiophene and thiophene. 3-Bromothiophene is one of the most important intermediates from which a wide variety of 3-substituted thiophenes are obtained, for example by means of Grignard reactions, by lithiation, or by oxidation. The use of 3-bromothiophene as the initial material in a production process is, however, hampered by the undesirable bromides formed as byproducts and by the difficult reaction conditions, such as an unsuitable temperature and an inert atmosphere.

The preparation of 3-substituted thiophenes by using an acyclic compound as the initial material has been studied extensively. These processes often have the disadvantage that they produce large amounts of 2-substituted thiophenes as by products. Some examples of these processes are the use of various mercaptans or thioethers as the initial material (Butler, A. R., Henry, J. B., J. Chem. Soc., B, 1970, or Campaigne, E., Monroe, P. A., J. Am. Chem. Soc., 76 (1954), 2445). 3-substituted thiophenes can also be prepared from other compounds which contain either double bonds or other functional groups (Veal, K. T., Grinter, T. J., EP 38121, or Duus, F., Tetrahedron, 32 (1976), 2817).

As mentioned above, many of these processes are known to those skilled in the art to produce large amounts of undesirable 2-substituted thiophene compounds and isomers, the separating of which causes difficulties. Furthermore, the undesirable byproducts are derived from the same initial material, and thus the yield will remain very low in the state-of-the-art processes.

SUMMARY OF THE INVENTION

The object the present invention is to provide a maximally selective process for the preparation of a 3-substituted $C_4$–$C_{18}$-alkylthiophene, the yield and the degree of purity being maximally high. The said objectives have now been achieved by a process wherein the preparation is carried out by allowing an alkali metal salt of a $C_4$–$C_{18}$-alkylsuccinic acid to react with a compound of sulfur and phosphorus in an organic solvent at a temperature of 100°–180° C., the resulting product being a 3-($C_4$–$C_{18}$-alkyl)thiophene.

A yield of nearly 75% is achieved by the process according to the invention, the degree of purity being approx. 95–98%. It is a further advantage of the invention that the final product is easily separated.

As regards the state of the art, it should further be pointed out that U.S. patent publication 2,658,903 discloses a process for the preparation of 3-alkylated thiophene from the corresponding alkali metal salt of an alkylsuccinic acid. According to the publication, however, only 3-methylthiophene and 3-ethylthiophene have been prepared, i.e. the alkyl substituents are different from those in the present invention, in addition to which the reaction has been carried out within a temperature range of 225°–300° C., preferably at 250° C., i.e. at a temperature substantially higher than in the present invention.

These and other objects and advantages according to the present invention are obtained by reacting first a $C_4$–$C_{18}$-alkylsuccinic acid anhydride with an alkali metal hydroxide to give the alkali metal salt of $C_4$–$C_{18}$-alkylsuccinic acid, and by reacting thereafter the said salt with a compound of sulfur and phosphorus so that the final product obtained will be a 3-($C_4$–$C_{18}$-alkyl)thiophene.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the present invention will become apparent to those skilled in the art from this detailed description.

DETAILED DESCRIPTION OF THE INVENTION

According to the present invention, the initial material in the preparation of 3-substituted thiophene may be maleic acid anhydride, the process consisting of the following steps:

a) $\alpha$-$C_4$–$C_{18}$-alkene is combined with the maleic acid anhydride so that $C_4$–$C_{18}$-alkenylsuccinic acid anhydride is obtained, b) the $C_4$–$C_{18}$-alkenylsuccinic acid anhydride is hydrogenated catalytically to form $C_4$–$C_{18}$-alkylsuccinic acid anhydride, c) the $C_4$–$C_{18}$-alkylsuccinic acid anhydride is reacted with an alkali metal hydroxide so that the alkali metal salt of $C_4$–$C_{18}$-alkylsuccinic acid is formed, and d) the alkali metal salt of $C_4$–$C_{18}$-alkylsuccinic acid is reacted with a compound of sulfur and phosphorus so that 3-($C_4$–$C_{18}$-alkyl)thiophene is obtained as the final product.

The present process differs substantially from that disclosed in U.S. publication 2,658,903, where in the preparation of 3-methylthiophene begins with the hydrogenation of the disodium salt of itaconic acid. The process of the present invention is described by the following reaction formula, wherein R=$C_1$–$C_{15}$-alkyl and MOH= alkali metal hydroxide. Tetraphosphorus decasulfide is indicated as the compound of sulfur and phosphorus.

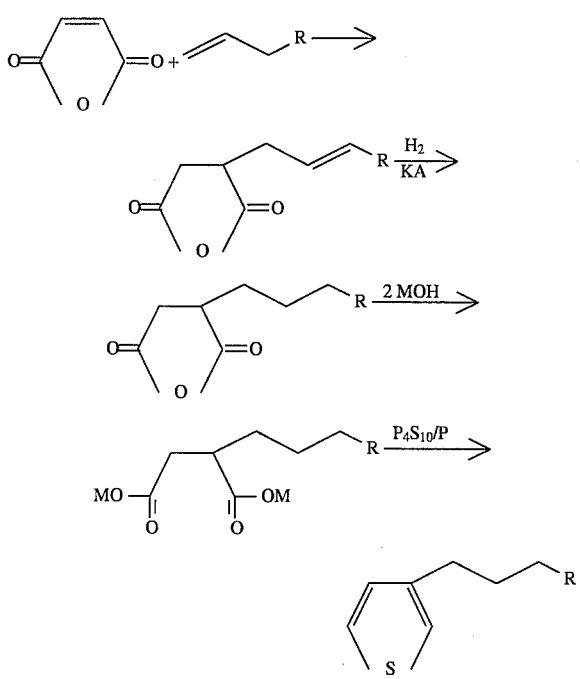

The compound of sulfur and phosphorus used in the process according to the invention is preferably tetraphosphorus decasulfide, $P_4S_{10}$. A high yield has been achieved with a mixture of tetraphosphorus decasulfide and red phosphorus, the molar ratio of the components in the mixture being 1:4–1:6, suitably 1:5.3. The molar ratio of the active compound of sulfur and phosphorus to the alkali salt of alkylsuccinic acid is suitably 0.5:1–2:1, most preferably approximately 0.5:1.

In the process according to the present invention, it is possible to use as the said organic solvent aliphatic or aromatic hydrocarbons or mixtures thereof, e.g. xylene, halogenated hydrocarbons, e.g. chloro- or dichlorobenzene, ethers, e.g. 2-ethoxyethyl ether, of mixtures of these. For example, o-dichlorobenzene is especially suitable.

In the process of the invention, the reaction temperature is preferably within the range 130°–180° C. The reaction time may vary between 1 and 20 hours. The reaction may occur in a normal atmosphere or under slight overpressure in an argon or nitrogen blanket.

After the reaction between the alkali salt of alkylsuccinic acid and the compound of sulfur and phosphorus has occurred, the solid precipitate is first removed, for example, by filtration or centrifugation. Thereafter the solvent is removed by distillation, and ultimately the 3-($C_4$–$C_{18}$-alkyl)thiophene obtained as the product is recovered by vacuum distillation. A washing or neutralization of the organic phase before the vacuum distillation is not necessary in the process of the invention.

The invention is illustrated below with the following non-limiting examples.

EXAMPLE 1

Alkenylsuccinic Acid Anhydride

Maleic acid anhydride (14 g, 0.14 mol) and 1-octene (50 ml, 0.32 mol) were loaded into an autoclave. The mixture was purged with nitrogen. The reaction mixture was heated at 210° C. for 4 hours. After cooling the mixture was filtered, and excess octene was evaporated out at reduced pressure. The yield of octenylsuccinic acid anhydride was 25 g (85% of the theoretical amount).

EXAMPLE 2

Alkenylsuccinic Acid Anhydride

The procedure followed was as described in Example 1, but the amount of octene was 30 ml (0.19 mol), whereupon the yield was 80% of the theoretical amount.

EXAMPLE 3

Alkylsuccinic Acid Anhydride

The octenylsuccinic acid anhydride was dissolved in ethyl acetate and was hydrogenated using a palladium/carbon catalyst (5% by weight of the initial material). The catalyst was filtered out, and the solvent was evaporated. The obtained yield of octylsuccinic acid was 24 g (95% of the theoretical amount).

EXAMPLE 4

Alkylsuccinic Acid Anhydride

The procedure followed was as described in Example 3, but dodecylsuccinic acid anhydride was used, which had been prepared by substantially the same procedure as used in Examples 1 and 2, and a palladium/carbon catalyst at 1% by weight. The yield was the same as in Example 3, i.e. 95% of the theoretical amount.

EXAMPLE 5

Potassium Salt of Alkylsuccinic Acid 254 g (1.2 mol) of octylsuccinic acid anhydride was mixed with 500 ml of ethanol, and the mixture was heated until the anhydride had dissolved. A solution of 134.6 g (2.4 mol) of potassium hydroxide in 1200 ml of ethanol was added to the solution. The solution was cooled slowly for several hours, whereafter the produced precipitate was filtered. The precipitate was dried in an oven at 40° C. The yield of the potassium salt of octylsuccinic acid was 275 g, which was 75% of the theoretical amount.

EXAMPLE 6

Disodium Salt of Alkylsuccinic Acid 143.1 g (0.675 mol) of octylsuccinic acid anhydride was mixed with 250 ml of ethanol, and the mixture was heated until the anhydride had dissolved. A solution of 54 g (1.35 mol) of sodium hydroxide in 675 ml of ethanol was added to the solution. The solution was cooled slowly for several hours, whereafter the produced precipitate was filtered. The precipitate was dried in an oven at 40° C. The yield of the disodium salt of octylsuccinic acid was 168.3 g, which was 91% of the theoretical amount.

EXAMPLE 7

2-Octylthiophene 22.9 g (0.075 mol) of the dipotassium salt of octylsuccinic acid, 16.6 g (0.0375 mol) of tetraphosphorus decasulfide, 9.3 g (0.3 mol) of red phosphorus and 100 ml of o-dichlorobenzene were charged into a 300 ml pressure reactor. Nitrogen was blown through the reactor for 1 hour, whereafter the reactor was closed. The reactor temperature was raised to 180° C., which was maintained for 3.5 hours. Thereafter the temperature was lowered to 40° C., and overpressure was removed from the reactor. Thereafter 150 ml of ether was added to the reaction mixture, and the inorganic precipitate was filtered out by suction. The filtrate was first washed with 50 ml of water, then neutralized with a 10% NaOH solution, and ultimately washed with water several times, until the ether solution was neutral. The organic solution was then dried with $Na_2SO_4$, whereafter the ether and the o-dichlorobenzene were distilled out at a slightly reduced pressure. Ultimately the product was distilled by means of a vacuum pump at a temperature of approx. 90° C. and a pressure of 1 mbar. The yield was 45%.

EXAMPLE 8

3-Dodecylthiophene

The reaction was carried out in substantially the same manner as in Example 7, by using 27.2 g (0.075 mol) of the dipotassium salt of dodecylsuccinic acid as the initial materials (the salt was prepared in the manner described in Example 5), 33.3 g (0.075 mol) of tetraphosphorus decasulfide, and 9.3 g (0.3 mol) of red phosphorus, as well as 100 ml of dichlorobenzene as a solvent. The yield of dodecylthiophene was 48% (b.p. 196° C./20 mbar).

EXAMPLE 9

3-Octylthiophene 160.3 g (0.525 mol) of the dipotassium salt of octylsuccinic acid, 116.9 g (0.263 mol) of tetraphosphorus decasulfide, 43.4 g (1.4 mol) of red phosphorus, and 600 ml of o-dichlorobenzene were charged into a 2000 ml Parr pressure reactor which was equipped with a mechanical stirrer and with inlet and outlet connections for the through-flow of nitrogen. The reactor was closed, the stirrer was started, and nitrogen was blown through the reactor for 1 hour. Thereafter the flow of nitrogen was cut off, and the reactor temperature was raised to approx. 150° C., at which it was kept for 4.5 hours. After cooling to 40° C. the overpressure was released.

The reaction mixture was treated by removing the inorganic precipitate by filtration. The precipitate was washed upon a filter with 600 ml of MTBE, which was used in four 150 ml portions. The filtrate was combined with the organic phase.

The combined organic phase was subjected to fractional distillation (a 15 cm VIGREAUX column). Most of the MTBE was distilled out at normal pressure, and the remainder, as well as the o-dichlorobenzene, at a reduced pressure of 40–70 mbar.

The crude product was thereafter subjected to fractional distillation at a pressure of approx. 1.5 mbar using the same fractional distillation column. The product obtained was 77.5 g of 3-octylthiophene having a purity of 94.4%, which corresponded to a yield of 71.1% as calculated from the theoretical yield.

EXAMPLES 10–17

3-Octylthiophene

The results from the reactions which were carried out substantially in accordance with the above Example 7 (Examples 10–13) and the above Example 9 (Examples 14–17) in pressure reactors of 300 ml and 2000 ml are presented in the following table. The initial material in Examples 10–12 and 14–16 was the dipotassium salt and in Examples 13 and 17 the disodium salt of octylsuccinic acid (HASA). The solvent used was o-dichlorobenzene (o-DCB), 2-ethoxyethyl ether, or products LI 200 and SOLVESSO 100.

TABLE

| Example | Initial | material | Time h | Temperature °C. | Solvent | Yield % | Purity % |
| --- | --- | --- | --- | --- | --- | --- | --- |
| 10 | HASA-K | 0.075 mol | 3.5 | 180 | o-DCB + Li200 (1:4) | 41.9 | 87 |
|  | $P_4S_{10}$ | 0.0375 mol |  |  |  |  |  |
|  | $P_4$ | 0.15 mol |  |  |  |  |  |
| 11 | HASA-K | 0.075 mol | 3.5 | 180 | SOLVESSO 100 | 51.3 | 94 |
|  | $P_4S_{10}$ | 0.0375 mol |  |  |  |  |  |
|  | $P_4$ | 0.15 mol |  |  |  |  |  |
| 12 | HASA-K | 0.075 mol | 3.5 | 180 | 2-ethoxyethyl- ether | 21.7 | 94 |
|  | $P_4S_{10}$ | 0.0375 mol |  |  |  |  |  |
|  | $P_4$ | 0.225 mol |  |  |  |  |  |
| 13 | HASA-Na | 0.075 mol | 3.5 | 180 | o-DCB | 57.1 | 98 |
|  | $P_4S_{10}$ | 0.075 mol |  |  |  |  |  |
|  | $P_4$ | 0.225 mol |  |  |  |  |  |
| 14 | HASA-K | 0.525 mol | 17 | 130–150 | o-DCB | 73.6 | 97 |
|  | $P_4S_{10}$ | 0.525 mol |  |  |  |  |  |
|  | $P_4$ | 2.1 mol |  |  |  |  |  |
| 15 | HASA-K | 0.525 mol | 5 | 160–170 | SOLVESSO 100 | 66.9 | 96 |
|  | $P_4S_{10}$ | 0.263 mol |  |  |  |  |  |
|  | $P_4$ | 1.4 mol |  |  |  |  |  |
| 16 | HASA-K | 0.525 mol | 5.5 | 160–170 | o-DCB + SOLVESSO 100 (1:4) | 66.5 | 95 |
|  | $P_4S_{10}$ | 0.263 mol |  |  |  |  |  |
|  | $P_4$ | 1.4 mol |  |  |  |  |  |
| 17 | HASA-Na | 0.525 mol | 4 | 160–170 | o-DCB | 67.1 | 95 |
|  | $P_4S_{10}$ | 0.263 mol |  |  |  |  |  |
|  | $P_4$ | 1.4 mol |  |  |  |  |  |

We claim:

1. A process for the preparation of a 3-($C_4$–$C_{18}$-alkyl)thiophene, comprising the following steps:

a) combining an α-$C_4$–$C_{18}$-alkene with maleic acid anhydride to produce a $C_4$–$C_{18}$-alkenylsuccinic acid anhydride;

b) catalytically hydrogenating the $C_4$–$C_{18}$-alkenylsuccinic acid anhydride to produce a $C_4$–$C_{18}$-alkylsuccinic acid anhydride;

c) reacting the $C_4$–$C_{18}$-alkylsuccinic acid anhydride with an alkali metal hydroxide, producing an alkali metal salt of a $C_4$–$C_{18}$-alkylsuccinic acid; and d) reacting the alkali metal salt of the $C_4$–$C_{18}$-alkylsuccinic acid with a mixture of tetraphosphorus decasulfide and phosphorus in an organic solvent at a temperature of 100°–180° C., and obtaining a 3-($C_4$–$C_{18}$-alkyl) thiophene.

2. The process according to claim 1, wherein the compound of sulfur and phosphorus comprises tetraphosphorus decasulfide.

3. The process according to claim 1, wherein the organic solvent is a chlorinated hydrocarbon.

4. The process according to claim 1, wherein the organic solvent is an aromatic hydrocarbon mixture having a boiling point within the range of 130°–210° C.

5. The process according to claim 1, wherein the temperature of the reaction d) between the alkali metal salt of the $C_4$–$C_{18}$-alkylsuccinic acid and the compound of sulfur and phosphorus in the organic solvent is within the range of 130°–180° C.

6. The process according to claim 1 wherein step d) further comprises d1) removing a solid precipitate after the reaction in step d) has occurred, d2) removing the organic solvent by distillation, and d3) recovering the 3-($C_4$–$C_{18}$-alkyl)thiophene as the product by vacuum distillation.

7. The process according to claim 1, wherein said 3-($C_4$–$C_{18}$-alkyl(thiophene is 3-octylthiophene.

8. The process according to claim 1, wherein the alkali metal hydroxide is selected from the group consisting of potassium hydroxide and sodium hydroxide.

9. The process according to claim 3, wherein said chlorinated hydrocarbon is o-dichlorobenzene.

10. The process according to claim 1, wherein the solvent is selected from the group consisting of aliphatic hydrocarbons, aromatic hydrocarbons, halogenated hydrocarbons, ethers, and mixtures thereof.

11. The process according to claim 1, wherein the reaction temperature of step d) is from 130° to 180° C., and the reaction time is between 1 hour and 20 hours.

12. The process according to claim 1, wherein step d) is carried out at atmospheric pressure.

13. The process according to claim 1, wherein step d) is carried out under an argon or nitrogen blanket.

14. The process according to claim 6, wherein step d1) comprises filtration or centrifugation.

15. The process according to claim 1, wherein said catalytic hydrogenation comprises hydrogenating on a palladium/carbon catalyst, and filtering said catalyst from the reaction mixture.

16. The process according to claim 1, wherein step c) further comprises c1) filtering a precipitate of the alkali metal salt and drying the precipitate in an oven.

17. The process according to claim 1, wherein said mixture of tetraphosphorus decasulfide and phosphorus comprises a mixture of tetraphosphorus decasulfide and red phosphorus.

18. A process for the preparation of a 3-($C_4$–$C_{18}$-alkyl)thiophene, comprising reacting an alkali metal salt of a ($C_4$–$C_{18}$-alkyl)thiophene with a compound of sulfur and phosphorus in an organic solvent at a temperature of 100° to 180° C.

19. The process according to claim 18, wherein the compound of sulfur and phosphorus comprises tetraphosphorus decasulfide.

\* \* \* \* \*